US006545186B2

(12) United States Patent
Giselbrecht et al.

(10) Patent No.: US 6,545,186 B2
(45) Date of Patent: Apr. 8, 2003

(54) PROCESS FOR THE PURIFICATION OF KETONES OBTAINED FROM THE CORRESPONDING TERPENES BY OZONOLYSIS AND REDUCTION

(75) Inventors: Karlheinz Giselbrecht, Pasching (AT); Josef Schaller, Linz (AT); Rudolf Hermanseder, Pennewang (AT); Klaus Reiter, Linz (AT)

(73) Assignee: DSM Fine Chemicals Austria Nfg GmbH & Co., KG, Linz (AT)

( * ) Notice: Subject to any disclaimer, the term of this patent is extended or adjusted under 35 U.S.C. 154(b) by 0 days.

(21) Appl. No.: 10/012,539

(22) Filed: Dec. 12, 2001

(65) Prior Publication Data

US 2002/0077510 A1 Jun. 20, 2002

(30) Foreign Application Priority Data

Dec. 14, 2000 (AT) .......................................... 2075/2000

(51) Int. Cl.$^7$ ....................... C07C 45/00; C07C 49/105; C07C 15/00
(52) U.S. Cl. ..................... 568/361; 568/366; 568/373; 568/374; 568/376; 568/377; 568/410; 585/407
(58) Field of Search ................................. 568/361, 366, 568/373, 374, 376, 377, 399, 403, 410; 585/807

(56) References Cited

U.S. PATENT DOCUMENTS

| 4,335,261 A | 6/1982 | Ueda |
| 4,769,464 A | 9/1988 | Sajtos |

FOREIGN PATENT DOCUMENTS

| EP | 0 034 738 | 9/1981 |
| EP | 0 147 593 | 7/1985 |

OTHER PUBLICATIONS

Patent Abstracts of Japan, vol. 9, No. 309 (C–318), Abstract of JP 60–146843 (1985).

*Primary Examiner*—Sreeni Padmanabhan
*Assistant Examiner*—Sikarl A. Witherspoon
(74) *Attorney, Agent, or Firm*—Wenderoth, Lind & Ponack, L.L.P.

(57) ABSTRACT

Improved, safe process for the purification of ketones obtained by ozonolysis and subsequent reduction of the corresponding terpenes, in which, after the ozonolysis and reduction of acyclic mono-, bi- or tricyclic terpenes with ozonizable double bonds, converting the resulting corresponding crude ketone into a high-purity ketone by means of steam distillation at atmospheric pressure or at reduced pressure, extraction of the steam distillate and subsequent distillation.

10 Claims, No Drawings

PROCESS FOR THE PURIFICATION OF KETONES OBTAINED FROM THE CORRESPONDING TERPENES BY OZONOLYSIS AND REDUCTION

The invention relates to an improved process by which terpenes can be converted into the corresponding ketones by means of ozonolysis, reduction and subsequent purification in a simple and safe manner.

Ketones derived from terpenes, such as, for example, nopinone, are used, for example, in the fragrance industry or in the synthesis of chiral pharmachemicals.

These ketones are prepared, in accordance with the prior art, for example by oxidation of the corresponding terpenes, such as, for example, ocimene, β-pinene, limonene, camphene, sapinene, etc. However, these oxidation methods are either multistage and thus rather complex or can only be carried out using heavy-metal-catalyzed oxidizing agents, such as, for example, $KMnO_4$, $OsO_4$, $RuCl_3/NaIO_4$, etc.

Also described is the preparation of such ketones by means of ozonolysis and reduction. However, the literature warns on more than one occasion against distillative purification of the resulting ketone and reports explosions at the end of the distillation. Thus, for example, in Chem. Abstr. 114:149283, it is described that explosions may arise during the synthesis of nopinone on a large scale. For example, the ozonization of β-pinene samples in $CH_2Cl_2/MeOH$, subsequent cooling and addition of AcOH and Zn, in order to destroy ozonides, and subsequent heating to room temperature led to a violent explosion. In Chem. Abstr. 114:128191, it is also pointed out that at the end of the vacuum distillation of crude nopinone, obtained by ozonolysis of β-pinene, the distillation apparatus exploded. J. Org. Chem., Vol. 56, No. 25, 1991 also makes reference to this risk of explosion. In this connection, it is generally assumed that the trigger of these explosions is a cyclic peroxide or tetroxide or an ozonide.

It was an object of the present invention to find a way by which ketones obtained by ozonolysis and reduction of the corresponding terpenes can be purified in a simple and safe manner without the risk of explosion.

Surprisingly, this object was achieved by carrying out a steam distillation after the ozonolysis and reduction.

Accordingly, the invention provides an improved, safe process for the purification of ketones obtained by ozonolysis and subsequent reduction of the corresponding terpenes, which comprises, after the ozonolysis and reduction of acyclic mono-, bi- or tricyclic terpenes with ozonizable double bonds, converting the resulting corresponding crude ketone into a high-purity ketone by means of steam distillation at atmospheric pressure or at reduced pressure, extraction of the steam distillate and subsequent distillation.

In the process according to the invention, a crude ketone is purified in a simple and, in particular, safe manner. The ketone to be purified is obtained by ozonolysis with subsequent reduction of the corresponding terpene.

Suitable starting compounds here are acyclic, mono-, bi- or tricyclic terpenes which have an ozonizable double bond. These are, for example, from the group of the acyclic terpenes ocimene, myrcene, etc. In the case of the mono-, bi- or tricyclic terpenes, suitable terpenes are preferably those which have an exocyclic double bond. These are, for example, β-phellandrene, (+)- or (−)-limonene, β-pinene, camphene, sabinene, limonene, etc.

Preference is given to mono- or bicyclic terpenes with an exocyclic double bond. Particular preference is given to bicyclic terpenes with an exocyclic double bond, particular preference being given to β-pinene.

The ozonization is carried out according to the prior art. The temperatures are between −80° C. to just below the explosion limit of the solvent used, i.e. depending on the solvent used, up to 100° C. The temperature is preferably −40 to +30 80° C., again depending on the solvent used, a temperature of from −20 to +50° in turn being particularly preferably maintained.

The reaction of the terpene is carried out in an organic solvent in which the starting compound is readily soluble.

Suitable solvents are, accordingly, alcohols, halogenated hydrocarbons, acids, esters or mixtures thereof.

Preferred solvents are $CH_2Cl_2$, acetic acid, lower aliphatic alcohols having 1 to 6 carbon atoms, such as methanol, ethanol, isopropanol, etc., the use of methanol and ethanol being particularly preferred.

The starting material concentration is, depending on the reaction conditions, between 0.1M and 2M, a maximum starting material concentration of 0.5M being preferred in order to prevent any mist formation which may arise in the case of some starting compounds, such as, for example, in the case of β-pinene. It is, however, possible to mix the fully ozonized peroxide-containing solution again with up to 0.5M starting material and to fully ozonize again without mist formation.

Ozone is used in an equimolar amount or in excess based on the terpene, or on the ozonizable double bond, preference being given to adding the equimolar amount of ozone. The use of an excess leads to ozone break-through at the end of the ozonolysis.

After the ozonolysis, the peroxide-containing solution is, again in accordance with the prior art, worked up catalytically with $H_2$ over a noble metal catalyst or by chemical reduction with, for example, sulfides. Preference is given to a catalytic hydrogenation. In this connection, it is only relevant that the peroxidic ozonolysis products are present in dissolved form in an organic diluent which is inert under the reaction conditions of the hydrogenation. Here, organic diluents are to be understood as meaning customary diluents used in the hydrogenation, such as, for example, aliphatic or aromatic, optionally halogenated hydrocarbons, such as pentane, hexane, cyclohexane, toluene, xylenes, methylene chloride, dichloroethane, chlorobenzenes, carboxylic esters, such as methyl acetate, ethyl acetate or butyl acetate, ethers, such as diethyl ether, diisopropyl ether, tetrahydrofuran, ketones, such as acetone, methyl butyl ketone, alcohols, such as methanol, ethanol, isopropanol. In the process according to the invention, preference is given to using peroxidic ozonolysis solutions in a lower aliphatic alcohol having 1 to 6 carbon atoms, particularly preferably in methanol or ethanol. It is particularly advantageous to carry out the hydrogenation in the same solvent as is used for the ozonolysis.

For practical implementation, a suspension of the catalyst in the alcohol used in the ozonization, preferably in methanol or ethanol, very preferably in methanol, is introduced into a hydrogenation reactor, and the solution obtained in the ozonization is fed in. Suitable catalysts are the noble metal catalysts customarily used for hydrogenations, which can be used in the form of powder catalysts with support materials or without support material. Preference is given to using palladium or platinum catalysts, in particular platinum catalysts without support material. In the case of powder catalysts, suitable support materials are, for example, carbon, aluminum, silica gel or kieselguhr. It is also possible to use monolithic catalysts. Preference is given to using platinum catalysts, such as, for example, an Adams catalyst. In the process according to the invention, the yields are per se independent of the amount of catalyst used, although it is advisable, in order to achieve a sufficient hydrogenation rate, to introduce said catalysts in noble metal amounts of from 0.01 to 5% by weight, preferably from 0.1 to 2% by weight, based on the total amount of ozonization products fed in per hour in each case.

The hydrogenation is continued until hydrogen absorption can no longer be detected. During the hydrogenation, up to at most equivalent amounts of hydrogen are consumed for the reduction of the ozonization products. The amount of hydrogen which can be used during the hydrogenation ranges from 0.7 mol equivalents up to one mole equivalent.

The hydrogenation in the process according to the invention is advantageously carried out under virtually pressureless conditions. Virtually pressureless conditions are understood here as meaning pressures of from 1 to about 3 bar, as is customary in the art, in order to prevent the penetration of air into the hydrogenation reactor. It is, however, also possible to carry out the hydrogenation at a pressure up to 20 bar and, as a result, to increase the hydrogenation rate, although the risk of byproduct formation increases.

The reductive cleavage generally proceeds exothermically and is carried out at temperatures of from −10 to +150° C., preferably at +10 to 70° C. and particularly preferably at temperatures in the range from +15 to 50° C..

During the hydrogenation, a pH of from 2 to 12, preferably from 8 to 11, is advantageously maintained. Since acidic byproducts may form during the course of the hydrogenation, a base, advantageously dilute sodium hydroxide solution or alcoholic KOH, may be metered in, where necessary, to maintain the desired pH.

When ozonolysis and hydrogenation have been carried out, the hydrogenation solution is worked up according to the invention.

For this, the resulting hydrogenation solution is, where necessary, firstly adjusted to a pH of from 4 to 8, preferably from 5 to 7, by adding a suitable inorganic or organic acid, such as, for example, sulfuric acid, HCl, formic acid, acetic acid, p-toluenesulfonic acid, etc., and concentrated to one third to one sixth by distilling off or evaporating off the solvent.

Then, according to the invention, the steam distillation is carried out at atmospheric pressure or at a reduced pressure of from 10 mbar to atmospheric pressure. Preference is given to carrying out the steam distillation at atmospheric pressure.

Here, steam is bubbled into the concentrated hydrogenation solution, a factor from 1:5 to 1:10 being preferred.

The still temperature carrying the atmospheric-pressure steam distillation is approximately 100 to 102° C., and the head temperature is approximately 90 to 97° C..

The end of the steam distillation is achieved when the distillate is single-phase. When the steam distillation is complete, a second water-insoluble organic phase separates out in the still container which comprises the substances which are responsible for the explosions described in the literature. In order to prevent the precipitation of these exothermic, non-steam-volatile substances, a virtually non-steam-volatile compound in which these harmful substances readily dissolve is preferably added to the mixture to be distilled. These are preferably strongly apolar, non-steam-volatile high-boiling substances. Particular preference is given to using white oil. The high-boiling compound is used in an amount of up to 30% by weight, preferably in an amount of from 5 to 10% by weight, based on the desired end product.

The resulting two-phase distillate is then extracted one to 5 times, preferably up to 3 times, with a suitable extractant. Suitable extractants here are apolar solvents, such as ethers, for example methyl tert-butyl ether (MtBE), ethyl acetate, toluene, hexane, etc. Preference is given to using MtBE.

Then, optionally after purification of the organic phases, the extractant is distilled off at atmospheric pressure or at a reduced pressure down to 20 mbar, preferably down to 10 mbar. The residue which is left behind, the desired ketone, is then purified by a subsequent vacuum or atmospheric-pressure distillation. The ketones prepared in this way, or isolated and purified according to the invention are obtained here in purities greater than 99% and in yields between 75 and 90% in a safe and simple manner, without the risk of explosions.

Particular preference is given to using the process according to the invention for the preparation of nopinone from β-pinene, where both the ozonolysis and also the hydrogenation are carried out in the same $C_1$–$C_6$-alcohol, preferably in methanol or ethanol.

EXAMPLE 1 a) Ozonolysis 2 liters of a 1.0M methanolic β-pinene peroxide solution were prepared by ozonolysis of a 1.0M methanolic β-pinene solution at −15° C., the ozone concentration in the oxygen/ozone gas stream being 60 g/m$^3$. The ozone consumption corresponded exactly to one mole equivalent (100% of theory).

b) Hydrogenation

The 2 l of 1.0M peroxide solution from the above ozonolysis was reduced at 20° C. and a pH of 10 with hydrogen at a pressure of 50 mbar above atmospheric over Pt (Adams). The alkali consumption to adjust the pH with 15% KOH in methanol was 11 ml/l of PO solution. The $H_2$ consumption was 85% of theory.

c) Workup 2 liters of methanolic hydrogenation solution were adjusted to pH 6 with dilute sulfuric acid and concentrated to 400 g on a rotary evaporator by evaporating off methanol at atmospheric pressure. The distillate still contained 4 g/l of nopinone. The resulting residue (suspension) was admixed with 400 g of water and 50 g of white oil (about 30% based on pinene used), and then the crude nopinone was steam-distilled at atmospheric pressure using the steam generator (still temperature 100° C. and head temperature 97° C.). The end of the steam distillation was reached when the distillate became single-phase and the content of nopinone was <1 g/l of distillate. A total of 2740 g of two-phase distillate were obtained. The residue from the steam distillation was two-phase, all of the explosive byproducts (exothermicity of the isolated explosive substances is about 2000 J/g) being dissolved in the white oil phase (even after cooling to room temperature). As a result of the dilution effect with white oil, the exothermicity in the white oil phase was only [illegible] . . . extraction of the two-phase distillate with 1000 ml of MtBE in each case (the main byproduct, formaldehyde, remains in the aqueous phase), the organic phases were separated off and combined, and all of the MtBE was distilled off at atmospheric pressure on a rotary evaporator. 225 g of crude nopinone (yield 81% of theory) with a GC content of 98% remained in the residue. In the printout of the TLC spectrum of the residue, exothermicity was no longer apparent. Vacuum distillation of the crude nopinone at 20 mbar and a still temperature of 130° gave 220 g of nopinone with a GC content of >99% (yield 79% of theory).

What is claimed is:

1. An improved process for the purification of ketones obtained by ozonolysis in an alcohol, halogenated hydrocarbon, an acid, an ester or in mixtures thereof, at a temperature between −80 and +100° C. and subsequent reduction in an aliphatic or aromatic, optionally halogenated, hydrocarbon, in a carboxylic ester, an ether, a ketone or an alcohol in the presence of a noble metal catalyst with hydrogen of the corresponding terpenes, which comprises, that the reaction solution obtained after the ozonolysis and reduction of acyclic mono-, bi- or tricyclic terpenes with ozonizable double bonds, which contains the resulting corresponding crude ketone, is firstly adjusted to a pH from 4 to 8 by adding an acid and then converting the crude ketone into a high-purity ketone by means of steam distillation at atmospheric pressure or at reduced pressure, extraction of the steam distillate and subsequent distillation.

2. The process as claimed in claim 1, wherein the starting compound used is a terpene selected from the group ocimene, myrcene, β-phellandrene, (+)- or (−)-limonene, β-pinene, camphene, sabinene and limonene.

3. The process as claimed in claim 1, wherein for the ozonolysis a starting material concentration between 0.1M and 2M is used.

4. The process as claimed in claim 1, wherein the reduction takes place by catalytic hydrogenation with 0.7 to 1 mol equivalents of hydrogen and at a pH between 2 and 12.

5. The process as claimed in claim 1, wherein after ozonolysis and hydrogenation have been carried out, the hydrogenation solution is adjusted to a pH between 5 and 7 by adding an organic or inorganic acid, and is concentrated to one third to one sixth of the original solution volume.

6. The process as claimed in claim 1, wherein the steam distillation is carried out at atmospheric pressure or at a reduced pressure of from 10 mbar to atmospheric pressure.

7. The process as claimed in claim 6, wherein a strongly apolar, non-steam-volatile, high-boiling substance is added to the reaction solution during the steam distillation in an amount of up to 30% by weight, based on the final product.

8. The process as claimed in claim 6, wherein the two-phase distillate obtained by the steam distillation is extracted 1 to 5 times with an extractant.

9. The process as claimed in claim 8, wherein the extractant is distilled off from the organic phase at atmospheric pressure or at a reduced pressure of from 20 mbar to atmospheric pressure.

10. The process as claimed in claim 1, wherein the crude ketone is, finally, purified by vacuum or atmospheric-pressure distillation, as a result of which the corresponding ketone is obtained in purities of more than 99% and in yields of 75 to 90%.

* * * * *